(12) United States Patent
Chen et al.

(10) Patent No.: US 10,319,093 B2
(45) Date of Patent: Jun. 11, 2019

(54) IMAGE PROCESSING APPARATUS, IMAGE PROCESSING METHOD, AND PROGRAM

(71) Applicant: CANON KABUSHIKI KAISHA, Tokyo (JP)

(72) Inventors: Bin Chen, Kawasaki (JP); Daisuke Furukawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 49 days.

(21) Appl. No.: 15/217,302

(22) Filed: Jul. 22, 2016

(65) Prior Publication Data

US 2017/0140534 A1 May 18, 2017

(30) Foreign Application Priority Data

Jul. 31, 2015 (JP) ................................. 2015-151611

(51) Int. Cl.
*G06K 9/00* (2006.01)
*G06T 7/00* (2017.01)
(Continued)

(52) U.S. Cl.
CPC .......... *G06T 7/0014* (2013.01); *A61B 5/7278* (2013.01); *A61B 5/742* (2013.01);
(Continued)

(58) Field of Classification Search
None
See application file for complete search history.

(56) References Cited

U.S. PATENT DOCUMENTS

| 7,697,742 B2 | 4/2010 | Dehmeshki | 382/131 |
| 8,103,077 B2 * | 1/2012 | Hong | G06T 7/12 382/128 |

(Continued)

FOREIGN PATENT DOCUMENTS

| JP | 2008-503294 | 2/2008 |
| JP | 2008-253293 | 10/2008 |

(Continued)

OTHER PUBLICATIONS

Yongqiang Tan, et al., "Segmentation of lung lesions on CT scans using watershed, active contours, and Markov random field", Medical Physics, vol. 40, No. 4, pp. 43502-1 to 43502-10 (Apr. 2013).

(Continued)

*Primary Examiner* — Shervin K Nakhjavan
(74) *Attorney, Agent, or Firm* — Venable LLP

(57) ABSTRACT

A boundary of a site included as an attached abnormal shadow in a medical image is corrected to allow assisting in diagnosis based on a shape of a tissue. An image processing apparatus according to the present invention includes: a boundary extraction unit configured to extract a boundary of a first site and a boundary of a second site in the medical image; a boundary identification unit configured to identify a partial boundary of the first site that is adhere to the boundary of the second site as a first boundary part, and to identify a partial boundary of the first site that is not adhere to the boundary of the second site as a second boundary part; and a correction unit configured to correct a shape of the first boundary part based on the second boundary part.

12 Claims, 13 Drawing Sheets

(51) Int. Cl.

| | | |
|---|---|---|
| *G06T 7/60* | (2017.01) | |
| *G06T 7/12* | (2017.01) | |
| *G06T 7/50* | (2017.01) | |
| *G06T 7/13* | (2017.01) | |
| *A61B 5/00* | (2006.01) | |
| *G06K 9/46* | (2006.01) | |
| *G06K 9/62* | (2006.01) | |

(52) U.S. Cl.
CPC .......... *A61B 5/7475* (2013.01); *G06K 9/4604* (2013.01); *G06K 9/62* (2013.01); *G06T 7/0012* (2013.01); *G06T 7/12* (2017.01); *G06T 7/13* (2017.01); *G06T 7/50* (2017.01); *G06T 7/60* (2013.01); *G06K 2209/05* (2013.01); *G06T 2207/10081* (2013.01); *G06T 2207/10088* (2013.01); *G06T 2207/20116* (2013.01); *G06T 2207/30064* (2013.01); *G06T 2207/30096* (2013.01)

(56) References Cited

U.S. PATENT DOCUMENTS

| | | | | |
|---|---|---|---|---|
| 8,870,779 | B2* | 10/2014 | Altmann | ................ A61B 5/062 |
| | | | | 382/128 |
| 9,449,247 | B2* | 9/2016 | Yamada | ................ G06T 11/60 |
| 9,761,041 | B2* | 9/2017 | Ogino | ..................... A61B 8/13 |
| 10,019,804 | B2 | 7/2018 | Akahori | ................ G06T 7/0081 |
| 2008/0181481 | A1 | 7/2008 | Hong et al. | ................... 382/132 |
| 2009/0238425 | A1 | 9/2009 | Matsumoto et al. | |
| 2010/0189320 | A1* | 7/2010 | Dewaele | ................ G06T 7/168 |
| | | | | 382/128 |
| 2015/0317799 | A1* | 11/2015 | Akahori | ................ G06F 19/00 |
| | | | | 382/128 |
| 2016/0035071 | A1* | 2/2016 | Yamada | ............. G06F 3/04845 |
| | | | | 345/647 |
| 2016/0086049 | A1 | 3/2016 | Yamada | ................ G06K 9/6267 |
| 2016/0098836 | A1* | 4/2016 | Yamato | ................... A61B 6/50 |
| | | | | 382/128 |

FOREIGN PATENT DOCUMENTS

| | | |
|---|---|---|
| JP | 2009-225990 A | 10/2009 |
| JP | 2014-135990 | 7/2014 |
| JP | 2014-241000 | 12/2014 |
| WO | 2014/113786 A1 | 7/2014 |

OTHER PUBLICATIONS

Satrajit Basu, "Developing Predictive Models for Lung Tumor Analysis", Graduate Thesis and Dissertations, http://scholarcommons.usf.edu/etd/3963 (Jan. 2012).

European Search Report dated Jan. 4, 2017 in European Application No. EP16181845.5-1906.

Office Action dated Oct. 9, 2018 in counterpart Japan Application No. 2015-151611, together with English translation thereof.

* cited by examiner

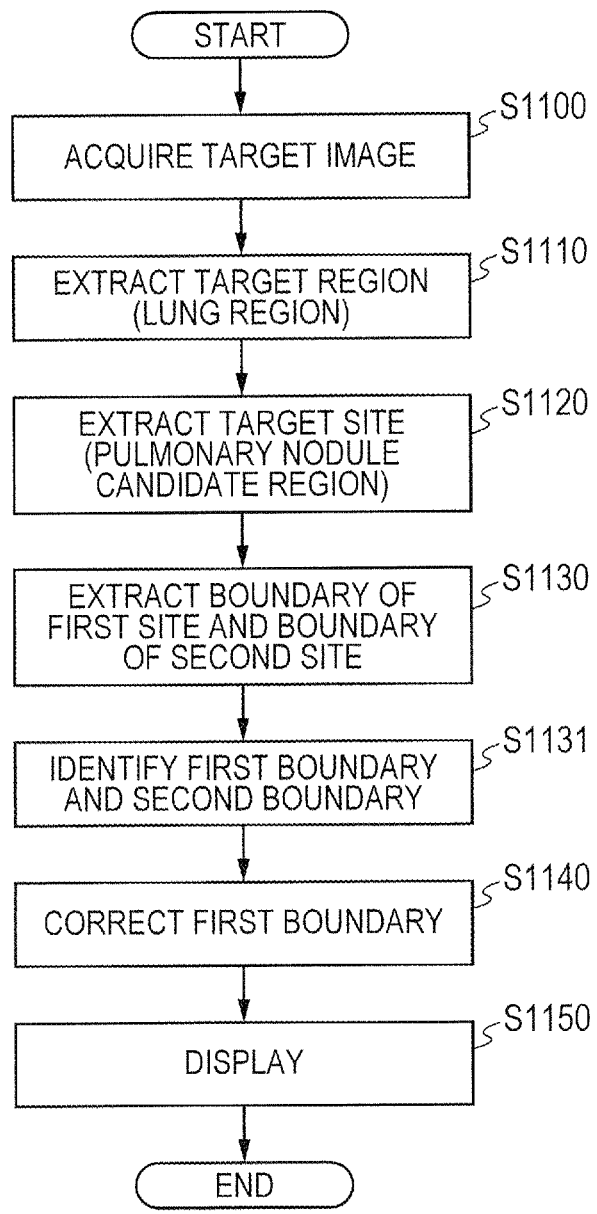

IMAGE PROCESSING APPARATUS, IMAGE PROCESSING METHOD, AND PROGRAM

BACKGROUND OF THE INVENTION

Field of the Invention

The present invention relates to an image processing apparatus, which is configured to process a medical image, an image processing method, and a program.

Description of the Related Art

In recent years, image quality of medical images taken by three-dimensional imaging device, such as an X-ray computed tomography apparatus (X-ray CT) and a magnetic resonance imaging device (MRI), has dramatically improved, and detailed information on the inside of a human body can now be obtained. However, the number of images has increased with the improvement in image quality, and a burden of reading the images on radiologists has increased. As a result, there is an increasing expectation for computer aided diagnosis (CAD).

It is particularly important to automatically detect an abnormal shadow region, which is highly likely to be an abnormal tissue, such as a tumor, or automatically distinguish benignancy and malignancy of an anatomical tissue. For example, in processing for automatically detecting an abnormal shadow region and processing for distinguishing benignancy and malignancy of a tissue by CAD, there is a need to calculate a shape feature amount representing a shape of a contour (boundary) of a site of a living body, which is an object, to thereby automatically calculate a likelihood of an abnormal shadow or automatically calculate malignancy of the tissue.

In the processing for distinguishing benignancy and malignancy of a pulmonary nodule, there have been reported that a lobulated contour (boundary) of the pulmonary nodule is one indicator of malignancy, and that a polygonal or polyhedral contour of the pulmonary nodule is one indicator of benignancy.

However, such an abnormal tissue is often included as a shadow (hereinafter referred to as "attached abnormal shadow") of a tissue (or site) in a state of being adhere to an organ or blood vessels in a medical image. Further, a surface (hereinafter referred to as "attached surface") that is adhere to the organ or blood vessels and a surface (hereinafter referred to as "non-attached surface") that is not adhere to the organ or blood vessels often have different shape feature amounts. A shadow of a tissue (or site) in a state of being not adhere to an organ or blood vessels is referred to as a "non-attached abnormal shadow".

Clinically, a medical doctor observes a contour (boundary) of a non-attached surface of an attached abnormal shadow to diagnose a tissue. Therefore, in calculating a shape feature amount of a region of the attached abnormal shadow by CAD, when the shape feature amount is calculated including a contour (boundary) of an attached surface, the calculated shape feature amount may differ from a shape feature amount of the contour (boundary) of the non-attached surface that the doctor wants to observe.

To address the above-mentioned problem, in Japanese Patent Application Laid-Open No. 2009-225990, there is disclosed a technology for calculating a circularity using a non-attached surface. Specifically, there is disclosed a technology of obtaining a plurality of nodes forming a polygonal line that approximates a contour of a nodular region, determining a position of a reference point, and calculating a circularity using areas of a plurality of regions determined based on the plurality of nodes and the reference point.

SUMMARY OF THE INVENTION

However, there are many shape feature amounts that need to be calculated from a closed curved surface (line), such as a feature amount of spherical harmonics (SPHARM) (for example, shape vector) and a feature amount based on a major diameter and a minor diameter of an approximate ellipsoid. In the technology disclosed in Japanese Patent Application Laid-Open No. 2009-225990, the circularity is calculated using the non-attached surface excluding the attached surface, and hence such feature amounts cannot be obtained. Further, in Japanese Patent Application Laid-Open No. 2009-225990, a center of gravity of a pulmonary nodule, which is to be used in the calculation of the circularity, is determined in a method similar to that for the region of the non-attached abnormal shadow, and hence there is a possibility that the center of gravity of the region of the attached abnormal shadow cannot be determined accurately.

It is an object of the present invention to provide an image processing apparatus, an image processing method, and a program, the image processing apparatus being capable of appropriately calculating a shape feature amount, which is to be used in computer aided diagnosis (including a technology for automatically detecting an abnormal shadow region and a technology for distinguishing benignancy and malignancy of a tissue), for a site included as an attached abnormal shadow in a medical image.

According to one embodiment of the present invention, there is provided an image processing apparatus, including: a boundary extraction unit configured to extract a boundary (entire boundary) of a first site and a boundary (entire boundary) of a second site in a medical image; a boundary identification unit configured to identify a partial boundary of the first site that is adhere to the boundary of the second site as a first boundary part, and to identify a partial boundary of the first site that is not adhere to the boundary of the second site as a second boundary part; and a correction unit configured to correct a shape of the first boundary part based on the second boundary part.

According to the present invention, a part of the boundary of the site included as the attached abnormal shadow in the medical image can be corrected to assist in diagnosis based on a shape of the tissue.

Further features of the present invention will become apparent from the following description of exemplary embodiments with reference to the attached drawings.

BRIEF DESCRIPTION OF THE DRAWINGS

FIG. 3 is a flow chart for illustrating processing executed by an image processing apparatus according to the first embodiment.

DESCRIPTION OF THE EMBODIMENTS

Preferred embodiments of the present invention will now be described in detail in accordance with the accompanying drawings.

First Embodiment

Now, an example of a first embodiment of the present invention is described in detail with reference to the drawings. An image processing apparatus according to this embodiment is configured to extract a candidate region (pulmonary nodule candidate region) of a pulmonary nodule, which is a site suspected to have a lung cancer (tumor), from a CT image (target image) of a target case, and to correct an attached surface (boundary surface that is adhere to a pleura) of a pulmonary nodule candidate region attached to the pleura. At this time, the image processing apparatus according to this embodiment is configured to identify the attached surface and a non-attached surface (boundary surface that is not adhere to the pleura) of the pulmonary nodule candidate region. Then, a shape of the attached surface is corrected based on a shape of the extracted non-attached surface.

In the following description, a case is described where a pulmonary nodule attached to a pleura on a chest CT image is a processing target, but a range of application of the present invention is not limited to a modality and a target, such as a pulmonary nodule or tumor, of this embodiment. The present invention is also applicable to another modality, such as MRI, and to sites, such as a cyst, an angioma, and hyperplasia other than the pulmonary nodule or tumor.

Figure 1:
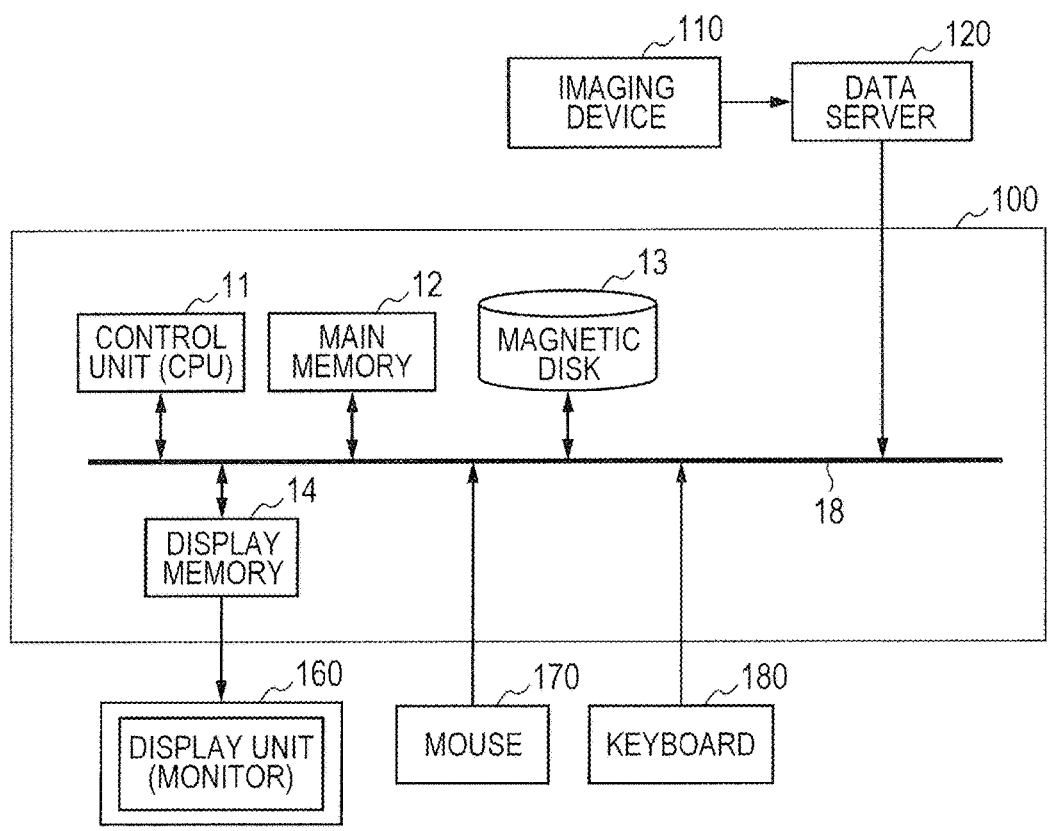
FIG. 1 is a diagram for illustrating a system configuration (image processing system) of an image processing apparatus according to the present invention and devices connected thereto.

Next, specific apparatus configuration, functional configuration, and processing flow are described. FIG. 1 is a diagram for illustrating a system configuration (image processing system) of the image processing apparatus according to this embodiment and devices connected thereto. The image processing system according to this embodiment includes an image processing apparatus 100, an imaging device 110, a data server 120, a display unit (monitor) 160, and input units (mouse 170 and keyboard 180).

The image processing apparatus 100 may be achieved with a personal computer (PC), for example, and includes a control unit (CPU) 11, a main memory 12, a magnetic disk 13, and a display memory 14. The control unit 11 is configured to mainly control operation of components of the image processing apparatus 100. The main memory 12 is configured to store a control program to be executed by the control unit 11, and to provide a work area for program execution by the control unit 11. The magnetic disk 13 is configured to store an operating system (OS), device drivers for peripheral devices, and various types of application software including a program for performing the processing to be described later.

The display memory 14 is configured to temporarily store display data for the display unit 160. The display unit 160 is a cathode ray tube (CRT) monitor or a liquid crystal monitor, for example, and is configured to display an image based on data from the display memory 14. The mouse 170 and the keyboard 180, which function as the input units, are used by a user to perform pointing input and input of characters and the like, respectively. Those components are communicably connected to one another by a common bus 18.

Figure 2:
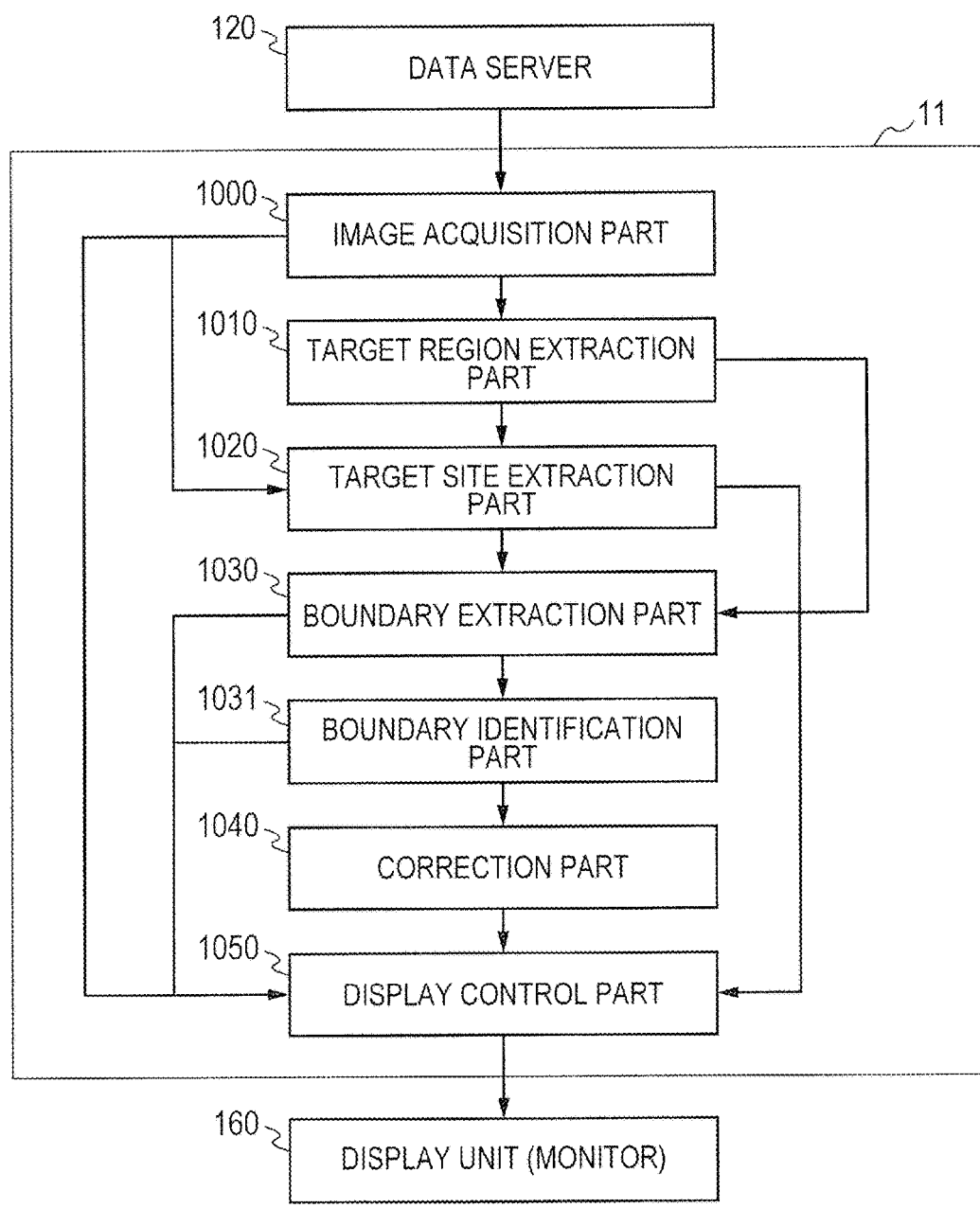
FIG. 2 is a diagram for illustrating a functional configuration of an image processing system including a control unit according to a first embodiment of the present invention.

FIG. 2 is a diagram for illustrating a functional configuration of the image processing system including the control unit 11 according to this embodiment. The control unit 11 according to this embodiment includes, as functional components, an image acquisition part 1000, a target region extraction part 1010, a target site extraction part 1020, a boundary extraction part 1030, a boundary identification part 1031, a correction part 1040, and a display control part 1050. Moreover, the control unit 11 is communicably connected to the data server 120 and the display unit 160.

The image processing apparatus 100 including the control unit 11 is configured to process a medical image, which is acquired by the imaging device 110, such as a computed tomography apparatus (CT), a magnetic resonance imaging device (MRI), or a radiography apparatus (digital radiography) configured to capture a two-dimensional radiation image. In this embodiment, description is given using a medical image (CT image) taken by a computed tomography apparatus (CT).

The imaging device 110 is configured to transmit the taken CT image to the data server 120. The data server 120 is configured to hold the image (CT image) taken by the imaging device 110. The image processing apparatus 100 is configured to read necessary data from the data server 120 via a network, such as a local area network (LAN), to thereby acquire image data stored in the data server 120.

Next, elements forming the control unit 11 of the image processing apparatus 100 are described. The image acquisition part 1000 in FIG. 2 is configured to acquire a CT image (hereinafter referred to as "target image") of a chest, which is associated with an object (target case) and is a target of the image processing apparatus 100, from the data server 120, and to load the CT image into the image processing apparatus 100.

The target region extraction part 1010 is configured to extract a target region including a target site as a target of diagnosis. For example, the target region extraction part 1010 is configured to extract, from the target image acquired by the image acquisition part 1000, a lung region including a pulmonary nodule, pleurae, pleural spaces, lung blood vessels, bronchi, and other such regions. The target site extraction part 1020 is configured to extract a target site (first site) and a site (second site) that is adhere to the target site in a medical image. For example, the target site extraction part 1020 is configured to extract, from the lung region extracted by the target region extraction part 1010, at least one region (pulmonary nodule candidate region), which is a site suspected to have a pulmonary nodule.

The boundary extraction part 1030 is configured to extract a boundary of the target site (first site) and a boundary of the site (second site) that is adhere to the target site in the medical image. For example, the boundary extraction part 1030 is configured to extract, based on information on the lung region extracted by the target region extraction part 1010 and information on the pulmonary nodule candidate region extracted by the target site extraction part 1020, a boundary of the pulmonary nodule candidate region and a boundary of a site, such as an organ or blood vessels, that is adhere to the pulmonary nodule candidate region. The boundary may be a boundary line or a boundary surface, or a collection of points forming the boundary line or the boundary surface.

The boundary identification part 1031 is configured to identify, as a first boundary part (attached part), a partial boundary of the target site (first site) that is adhere to the boundary of the site (second site) that is adhere to the target site. Then, the boundary identification part 1031 is configured to identify, as a second boundary part (non-attached part), a partial boundary of the target site (first site) that is not adhere to the boundary of the site (second site) that is adhere to the target site. For example, the boundary identification part 1031 is configured to identify an attached surface and a non-attached surface of the pulmonary nodule candidate region.

The correction part 1040 is configured to correct a shape of the attached part (first boundary part) of the target site based on the non-attached part (second boundary part) of the target site. For example, the correction part 1040 is configured to correct a shape of the attached surface based on information on the non-attached surface of the pulmonary nodule candidate region, which has been identified by the boundary identification part 1031. The display control part 1050 is configured to output, to the display unit 160, information, such as coordinates and an instruction to change a display format, on the target site (first site), the site (second site) that is adhere to the target site, the attached part (first boundary part) of the target site before and after the correction, and the non-attached part (second boundary part) of the target site.

For example, the display control part 1050 is configured to output, to the display unit 160, the information on the pulmonary nodule candidate region extracted by the target site extraction part 1020, the site that is adhere to the pulmonary nodule candidate region, the attached surface and the non-attached surface of the pulmonary nodule candidate region, which have been identified by the boundary identification part 1031, and the attached surface corrected by the correction part 1040. The display unit 160 is configured to display, based on the information, the target site (first site), the site (second site) that is adhere to the target site, the attached part (first boundary part) of the target site before and after the correction, and the non-attached part (second boundary part) of the target site.

Next, operation of the image processing apparatus 100 is described in detail with reference to FIG. 3. FIG. 3 is a flow chart for illustrating processing executed by the image processing apparatus 100 according to this embodiment. This embodiment is realized by the control unit 11 executing a program (program for achieving the functional configuration of the image processing apparatus 100) stored in the main memory 12. Moreover, results of processing performed by the image processing apparatus 100 are stored in the main memory 12 to be recorded.

Moreover, the present invention may also be realized by supplying the program for achieving the functional configuration of the image processing apparatus 100 to the system or the apparatus via a network or a recording medium, and allowing one or more processors in a computer of the system or the apparatus to read and execute the program. Further, the present invention may also be realized by a circuit (for example, an application specific integrated circuit: ASIC) that is configured to achieve one or more functions.

<Step S1100>

In Step S1100, the image acquisition part 1000 acquires a target image. The image acquisition part 1000 executes processing of acquiring, as the target image, a CT image of a target case from the data server 120, and developing and holding the CT image on the main memory 12 of the image processing apparatus 100.

The target image in this embodiment is formed of a plurality of pixels, which are identifiable by components in directions of three orthogonal axes (x, y, and z), and a pixel size as additional information is defined for each of the three axis directions. In this embodiment, an exemplary case is described where respective pixel sizes in the three axis directions are specifically r_size_x=1.0 mm, r_size_y=1.0 mm, and r_size_z=1.0 mm. A density value (pixel value) of the target image may be regarded as a function derived with reference to a pixel address in a three-dimensional array of pixels.

In this embodiment, the target image is expressed as a function $I(x,y,z)$. The function $I(x,y,z)$ is a function using three-dimensional real-space coordinate values (x,y,z) in an imaging region of the target image as arguments to express a pixel value at the position.

<Step S1110>

In Step S1110, the target region extraction part 1010 extracts a target region (lung region). The target region extraction part 1010 extracts a region including an air region, a part of a bronchial region, a part of a lung blood vessel region, and the pulmonary nodule candidate region, that is, a region anatomically recognized as a lung field.

The target region extraction part 1010 is capable of automatically extracting a lung region $V_{lung}$ from the function $I(x,y,z)$ using a method using thresholding, region extension processing, level sets, or an organ atlas (model) based on anatomy, for example. Alternatively, a user may make a manual modification or adjustment to the lung region $V_{lung}$ via the mouse 170.

<Step S1120>

In Step S1120, the target site extraction part 1020 extracts a target site (pulmonary nodule candidate region) and a site, such as an organ or blood vessels, that is adhere to the target site. The target site extraction part 1020 extracts, from the lung region $V_{lung}$ extracted in Step S1110, at least one pulmonary nodule candidate region based on a density value (pixel value) or a shape having a feature of the pulmonary nodule candidate region.

The target site extraction part 1020 detects the pulmonary nodule candidate region from the lung region $V_{lung}$ using a technology such as filtering for emphasizing a blob structure based on the thresholding or an eigenvalue of a Hessian matrix. Then, the target site extraction part 1020 extracts the pulmonary nodule candidate region more finely using an active contour model, such as level sets and snakes, graph cuts, and other such technologies on the detected pulmonary nodule candidate region.

Alternatively, the target site extraction part 1020 may extract the target site based on a particular pulmonary nodule candidate region specified by a user via the mouse 170. In this case, the user uses the mouse 170 to obtain, as a seed point, coordinates belonging to the pulmonary nodule candidate region by referring to axial, sagittal, and coronal images of the target image displayed on the display unit 160.

The target site extraction part 1020 extracts at least one target site by the level sets, the graph cuts, the active contour model, and other such technologies using information on the obtained seed point, information on the lung region $V_{lung}$, and information on the density value (pixel value) or the shape having the feature of the pulmonary nodule candidate region.

Sites that are adhere to the pulmonary nodule (target site) include a pleura region, a blood vessel region, and the like. The pleura region is adhere to the lung region, and hence when the target region is adhere to the pleura region, the lung region $V_{lung}$ may be acquired as the site (second site) that is adhere to the target site (first site). When the target site is adhere to blood vessels, there is a need to extract the blood vessel region in advance to be acquired as the second site. The blood vessel region may be extracted from the lung region $V_{lung}$ by the active contour model, such as the level sets and the snakes, the graph cuts, and other such technologies based on a density value (pixel value) or a shape having a feature of the blood vessel region.

<Step S1130>

In Step S1130, the boundary extraction part 1030 extracts a boundary of the target site (first site) and a boundary of the site (second site) that is adhere to the target site. In this embodiment, a case is described where the second site is the lung region $V_{lung}$.

Here, a pulmonary nodule candidate region, which is the target site extracted by the target site extraction part 1020, is denoted by $V_{nodule}$. The boundary extraction part 1030 extracts a boundary surface $S_{nodule}$ of the pulmonary nodule candidate region (first site) $V_{nodule}$, which is formed of a collection or series of boundary pixels of the pulmonary nodule candidate region $V_{nodule}$. Specifically, the boundary extraction part 1030 extracts the boundary surface $S_{nodule}$ by detecting pixels demarcating the pulmonary nodule candidate region $V_{nodule}$ and a background in the pulmonary nodule candidate region $V_{nodule}$. Moreover, the boundary extraction part 1030 similarly extracts a boundary surface $S_{lung}$ of the lung region $V_{lung}$ (second site), which is formed of a collection or series of boundary pixels of the lung region $V_{lung}$.

<Step S1131>

In Step S1131, the boundary identification part 1031 identifies an attached part (first boundary part) and a non-attached part (second boundary part) of the target site. The boundary identification part 1031 identifies an attached surface $S_{attached}$ and a non-attached surface $S_{non-attached}$ of the pulmonary nodule candidate region $V_{nodule}$ based on the boundary surface $S_{nodule}$ of the pulmonary nodule candidate region $V_{nodule}$ and the boundary surface $S_{lung}$ of the lung region $V_{lung}$, which have been extracted in Step S1130.

Here, the attached surface (first boundary part) $S_{attached}$ is a surface at which the boundary surface $S_{nodule}$ of the pulmonary nodule candidate region (first site) $V_{nodule}$ is adhere to the boundary surface $S_{lung}$ of the lung region $V_{lung}$ (second site). Moreover, the non-attached surface (second boundary part) $S_{non-attached}$ is a surface at which the boundary surface $S_{nodule}$ of the pulmonary nodule candidate region (first site) $V_{nodule}$ is not adhere to the boundary surface $S_{lung}$ of the lung region $V_{lung}$ (second site).

The boundary surface $S_{lung}$ of the lung region $V_{lung}$ is adhere to the pleura region, and hence the attached surface $S_{attached}$ of the pulmonary nodule candidate region $V_{nodule}$ may be regarded as a portion at which the pulmonary nodule candidate region $V_{nodule}$ is adhere to the pleura region. In other words, the pulmonary nodule candidate region $V_{nodule}$ with the attached surface $S_{attached}$ is included as an attached abnormal shadow in the medical image. In contrast, the pulmonary nodule candidate region $V_{nodule}$ without the attached surface $S_{attached}$ is a solitary pulmonary nodule candidate region, and is included as a non-attached abnormal shadow in the medical image.

Figure 4A:
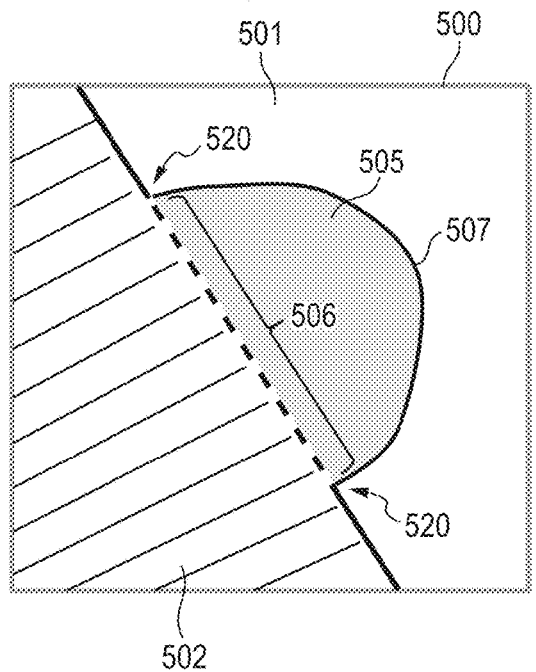
FIG. 4A is a diagram for illustrating an example of a first boundary part.
Figure 4B:
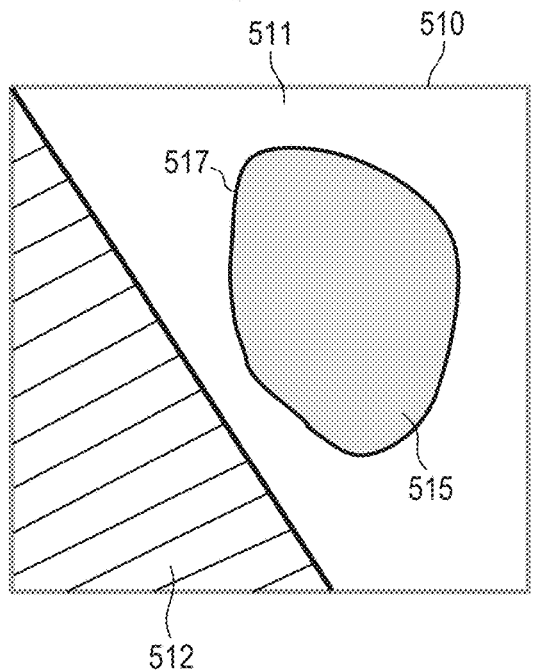
FIG. 4B is a diagram for illustrating an example of a second boundary part.

FIG. 4A and FIG. 4B are diagrams for illustrating examples of an attached surface (first boundary part) and non-attached surfaces (second boundary parts). Cross sections are used to simplify the description. In FIG. 4A, a pulmonary nodule candidate region 505, which is attached to a pleura, is illustrated. In FIG. 4B, a pulmonary nodule candidate region 515 of a solitary pulmonary nodule, which is not attached to the pleura, is illustrated.

A boundary surface of the pulmonary nodule candidate region 505 is formed of an attached surface (first boundary part) 506, which is indicated by the broken line, and a non-attached surface (second boundary part) 507, which is indicated by the solid line. A boundary surface of the pulmonary nodule candidate region 515 of the solitary pulmonary nodule is formed of a non-attached surface 517. The boundary identification part 1031 identifies the attached surface (first boundary part) 506 and the non-attached surface (second boundary part) 507. Moreover, the boundary identification part 1031 identifies the non-attached surface 517.

<Step S1140>

In Step S1140, the correction part 1040 corrects a shape of the attached surface (first boundary part) 506 based on the non-attached surface (second boundary part) 507. The correction part 1040 corrects the shape of the attached surface 506 of the pulmonary nodule candidate region 505 using the pulmonary nodule candidate region 505, which has been extracted in Step S1120, and information (attached/non-attached-surface information) on the attached surface 506 and the non-attached surface 507, which have been extracted in Step S1131. For the pulmonary nodule candidate region 515 of the solitary pulmonary nodule, no attached surface $S_{attached}$ is identified, and hence the correction part 1040 does not perform processing of correcting the boundary of the pulmonary nodule candidate region 515.

The correction part 1040 corrects (deforms) the shape of the attached surface 506 based on a shape feature of the non-attached surface 507 of the pulmonary nodule candidate region 505. For example, the correction part 1040 corrects (deforms) the shape of the attached surface (first boundary part) 506 using the active contour model that is based on a shape (for example, curvature) of at least a part of the non-attached surface (second boundary part) 507. In this embodiment, the attached surface 506 is corrected by being subjected to boundary surface propagation processing by a level set method, which is an active contour model.

The level set method is a phase-variable active contour model, and may be used to deform (propagate) a contour (boundary) to an ideal shape or position by using a cost function based on a feature amount representing a shape of the contour or a texture of a region.

Specifically, in the level set method, a space (high-dimensional space) that is one dimension higher is constructed for a target space, and a contour of a target is regarded as a cross section (zero iso-surface $\varphi=0$) of an implicit function $\varphi$ defined in the high-dimensional space. The contour (zero iso-surface $\varphi=0$) of the target is deformed while a shape of the implicit function $\varphi$ is moved along with time t. Therefore, when the implicit function $\varphi$ is designed appropriately depending on a target shape feature (target region) of deformation of the target, a change in topology of the contour (boundary) of the target and occurrence of a singular point may be addressed.

In the level set method, in order to change a shape of the zero iso-surface, a speed of motion (movement) is given to a point belonging to the implicit function $\varphi$ to propagate the implicit function $\varphi$ with elapse of time t. This may generally be expressed with the following expression (1).

$$\varphi_t = -F \cdot |\nabla \varphi| \quad (1)$$

In the expression (1), F represents a velocity function (cost function). The speed of motion of the point belonging to the implicit function $\varphi$ is determined by the velocity function F. In general, the velocity function F is designed in consideration of a texture or the shape feature of the target on the image so that the speed becomes lower, that is, the cost becomes larger as the zero iso-surface becomes farther from the contour of the target region, and so that the speed becomes higher, that is, the cost becomes smaller as the zero iso-surface becomes closer to the contour of the target region. Moreover, the velocity function F is designed so that the zero iso-surface is extended when the zero iso-surface is inside the target region, and so that the zero iso-surface is reduced when the zero iso-surface is outside the target region.

In this embodiment, the correction part 1040 corrects (deforms) the attached surface 506 so that a shape feature of the attached surface 506 approaches a shape feature of the non-attached surface 507 while maintaining smoothness of the contour (boundary) at points 520 of contact between the attached surface 506 and the non-attached surface 507. Clinical findings suggest that growth of a pulmonary nodule region stops at the attached surface, and hence the attached surface has a shape that is different from that of the non-attached surface. Therefore, the correction part 1040 performs correction to extend the attached surface. In this embodiment, the attached surface 506 is extended using a velocity function $F_\kappa(i,j,k)$ based on the curvature, which is expressed by the following expression (2).

$$F_\kappa(i,j,k) = 1 - e^{\alpha \cdot |\kappa(i,j,k) - \kappa_0|} \quad (2)$$

Here, a pixel (i,j,k) is a pixel (neighboring pixel) that is located outside the boundary surface $S_{nodule}$ (attached surface 506 and non-attached surface 507) of the pulmonary nodule candidate region 505 and is adjacent to the attached surface 506, and is a pixel (extension candidate pixel) for extending the attached surface 506.

In the expression (2), (i,j,k) represents a coordinate position of the pixel. Moreover, $\kappa(i,j,k)$ represents a curvature at the pixel (i,j,k), and is calculated by a signed distance function with the zero iso-surface $\varphi=0$ being a foreground. Further, $\kappa_0$ represents a curvature feature amount of the non-attached surface 507, and is an average (average curvature) of curvatures at respective pixels on the non-attached surface 507, for example. Alternatively, $\kappa_0$ may be a curvature at a pixel closest to the pixel (i,j,k) of a collection of reference pixels, the reference pixels being pixels on the non-attached surface 507 that is adhere to the attached surface 506.

In the expression (2), $\alpha$ ($\alpha<0$) is a weight coefficient. With the velocity function $F_\kappa(i,j,k)$, as a difference between the curvature $\kappa(i,j,k)$ at the pixel (i,j,k) and $\kappa_0$ becomes larger, speeds $F_\kappa$ at extension candidate pixels become higher, and a degree of extension of the first boundary part (attached surface 506) becomes higher. In contrast, as the difference between the curvature $\kappa(i,j,k)$ at the pixel (i,j,k) and $\kappa_0$ becomes smaller, the speeds $F_\kappa$ at the extension candidate pixels become lower to approach to 0, and the degree of extension of the first boundary part (attached surface 506) becomes lower.

In order to extend the first boundary part (attached surface 506) more efficiently and make the extension easier to control, a limitation expressed by the following expression (3) may be added.

$$N_{attached} \leq \beta \cdot N_{non\text{-}attached} \quad (3)$$

In the expression (3), $\beta$ represents a coefficient. $N_{attached}$ represents the number of pixels of the first boundary part (attached surface 506). $N_{non\text{-}attached}$ represents the number of pixels of the second boundary part (non-attached surface 507). With the expression (3), the number of pixels of the first boundary part (attached surface 506), which is extended by the correction, may be limited based on the number of pixels of the second boundary part (non-attached surface 507) to avoid infinite extension of the first boundary part (attached surface 506).

Figure 5A:
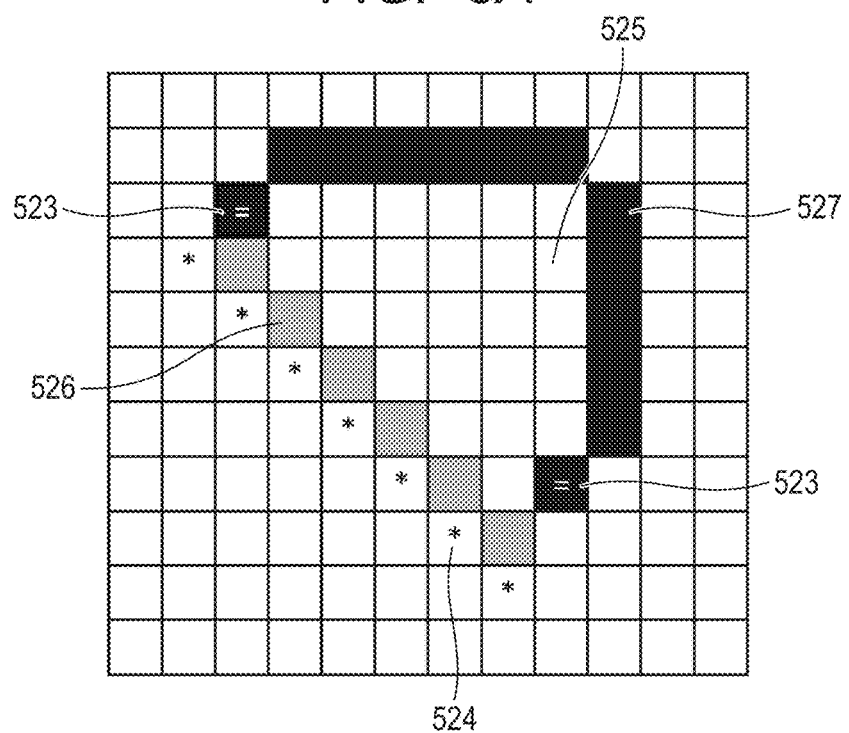
FIG. 5A is a diagram for illustrating an example of the first boundary part.
Figure 5B:
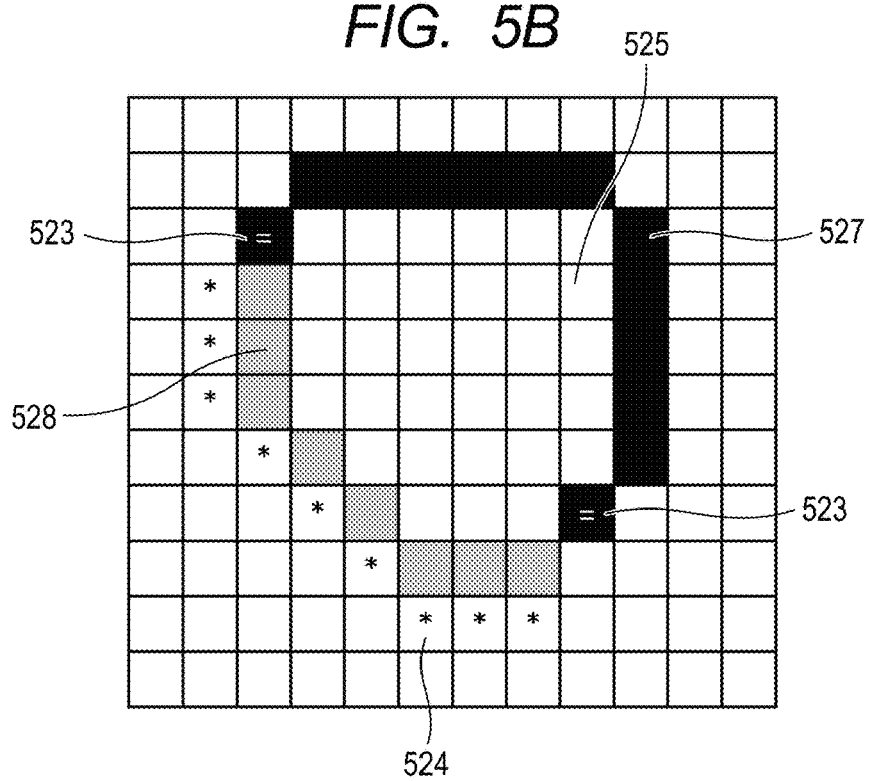
FIG. 5B is a diagram for illustrating a first example of correction of the first boundary part by a velocity function.
Figure 5C:
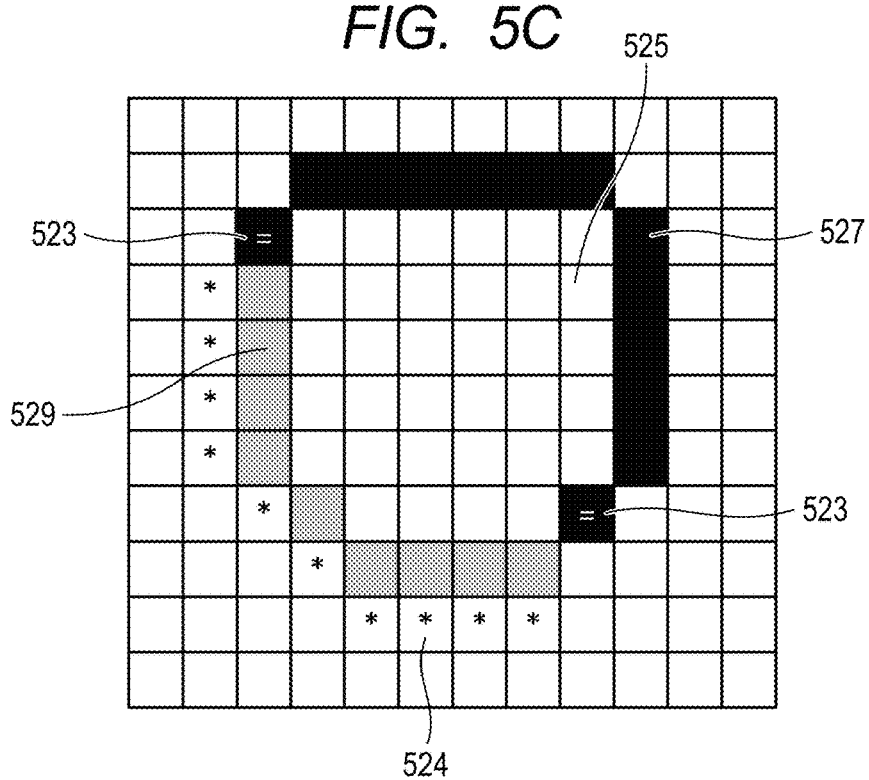
FIG. 5C is a diagram for illustrating a second example of correction of the first boundary part by the velocity function.

FIG. 5A to FIG. 5C are diagrams for illustrating an example of correction of the first boundary part (attached surface) by the velocity function $F_\kappa(i,j,k)$. In this example, one of an average curvature at pixels (pixels indicated by black) of the non-attached surface 527 and a curvature at one of reference pixels 523 (pixels indicated by "=") is $\kappa_0$. Neighboring pixels of pixels (pixels indicated by gray) of the attached surface 526 are extension candidate pixels 524 (pixels indicated by "*") (FIG. 5A).

The correction part 1040 calculates differences between curvatures $\kappa(i,j,k)$ and $\kappa_0$ at the extension candidate pixels 524, and the attached surface 526 is extended to an attached surface 528 in order from a pixel having the largest difference (FIG. 5B). This processing is repeated to extend the attached surface 528 to an attached surface 529 (FIG. 5C). As the speeds $F_\kappa$ at the extension candidate pixels become lower to approach to 0, and there is no need to further extend the attached surface 529, the correction (extension) of the attached surface 526 ends. The correction part 1040 sets the attached surface 529 obtained at the end of the correction processing as an attached surface after the correction.

Alternatively, the correction part 1040 may correct the shape of the attached surface (first boundary part) based on at least one of an approximate curve approximating the non-attached surface (second boundary part), an approximate curved surface approximating the non-attached surface (second boundary part), a symmetrical image of the non-attached surface (second boundary part), or a rotated image of the non-attached surface (second boundary part).

Figure 6A:
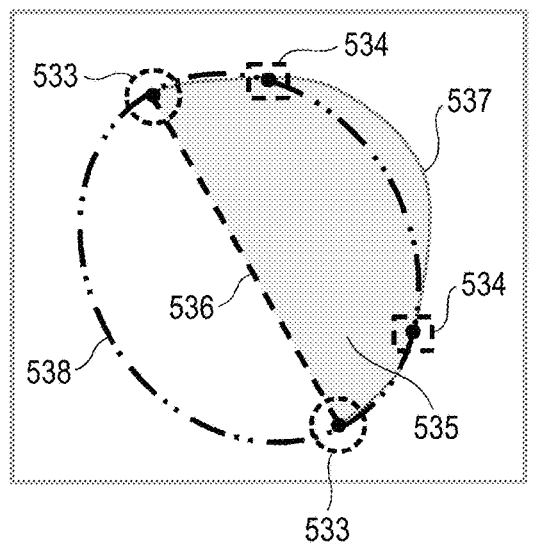
FIG. 6A and FIG. 6B are diagrams for illustrating correction of a shape of the first boundary part with an approximate ellipsoid.
Figure 6B:
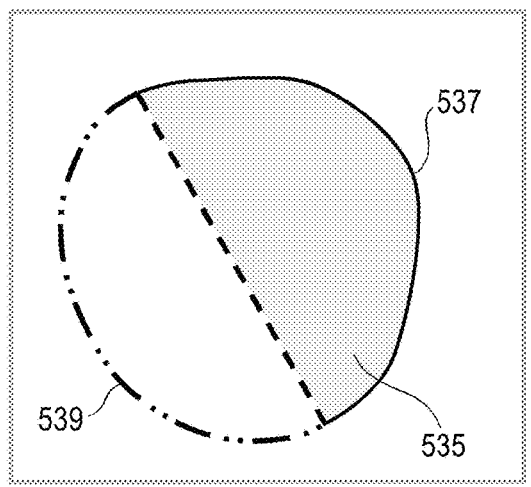

For example, the correction part 1040 may correct the shape of the attached surface (first boundary part) using ellipsoid fitting and other such technologies with an approximate ellipsoid (approximate curved surface) approximating the non-attached surface (second boundary part). FIG. 6A and FIG. 6B are diagrams for illustrating correction of the shape of the attached surface (first boundary part) with the approximate ellipsoid (approximate curved surface). As illustrated in FIG. 6A and FIG. 6B, the correction part 1040 calculates an approximate ellipsoid E(x,y,z) including reference pixels 533, the reference pixels 533 being pixels on a non-attached surface 537 that is adhere to an attached surface 536.

In this case, the correction part 1040 may further select one or more pixels as reference pixels 534 from the non-attached surface 537 to calculate the approximate ellipsoid E(x,y,z) including the reference pixels 533 and the reference pixels 534. Alternatively, the correction part 1040 may calculate the approximate ellipsoid E(x,y,z) by a least squares error method based on the reference pixels 533 and the reference pixels 534. The correction part 1040 sets a part (boundary) of an approximate ellipsoid 538 on the attached surface side of the reference pixels 533 as an attached surface 539 after the correction.

<Step S1150>

In Step S1150, the display unit 160 displays at least one piece of information, such as coordinates and an instruction to change a display format, on the target site (first site), the site (second site) that is adhere to the target site, the attached part (first boundary part) of the target site before and after the correction, and the non-attached part (second boundary part) of the target site. In this case, the display control part 1050 transmits, to the display unit 160, information on the pulmonary nodule candidate region (first site), the lung region (second site), the attached surface (first boundary part) before and after the correction, and the non-attached surface (second boundary part).

The display control part 1050 may superimpose those pieces of information, such as the image, on the medical image, such as the CT image, for display on the display unit 160. In this case, the display control part 1050 may generate a three-dimensional medical image on which those pieces of information are superimposed by volume rendering for display on the display unit 160. Alternatively, the display control part 1050 may generate a predetermined cross-sectional image of the superimposed three-dimensional medical image for display on the display unit 160.

As described above, according to this embodiment, the image processing apparatus 100 may identify the attached surface and the non-attached surface of the site included as the attached abnormal shadow in the medical image, and correct the attached surface based on features of the attached surface and the non-attached surface. As a result, a shape feature amount, which is to be used in computer aided diagnosis (including a technology for automatically detecting an abnormal shadow region and a technology for distinguishing benignancy and malignancy of a tissue), may be appropriately calculated for a site suspected to be an abnormal tissue, which can contribute to improvement in performance of the computer aided diagnosis.

The first embodiment is described above. However, the present invention is not limited thereto, and modifications and alterations may be made within the scope defined in the claims. For example, the correction part 1040 may correct the shape of the attached surface (first boundary part) based on at least one of a symmetrical image (mirror image) of the non-attached surface (second boundary part) or a rotated image of the non-attached surface (second boundary part) in addition to the approximate curve and the approximate curved surface.

Figure 7A:
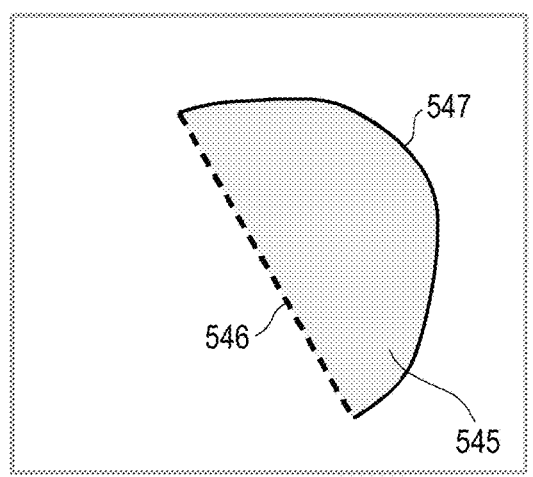
FIG. 7A and FIG. 7B are diagrams for illustrating an example in which the shape of the first boundary part is corrected based on a symmetrical image of the second boundary part.
Figure 7B:
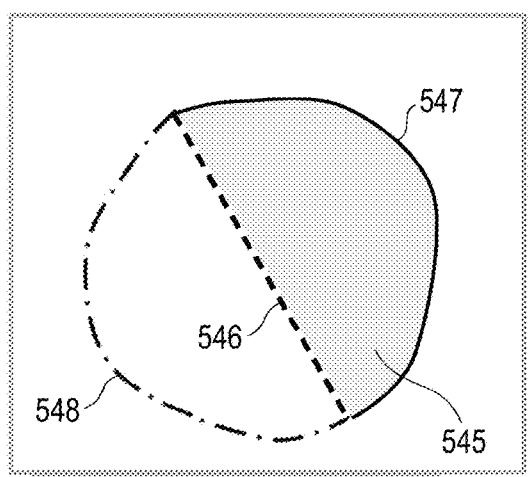

FIG. 7A and FIG. 7B are diagrams for illustrating an example in which the shape of the attached surface (first boundary part) is corrected based on the symmetrical image of the non-attached surface (second boundary part). The correction part 1040 sets a surface obtained by approximating the attached surface 546 with a plane as a plane of symmetry to generate a symmetrical image of the non-attached surface 547, and sets the generated symmetrical image as an attached surface 548 after the correction.

Figure 8A:
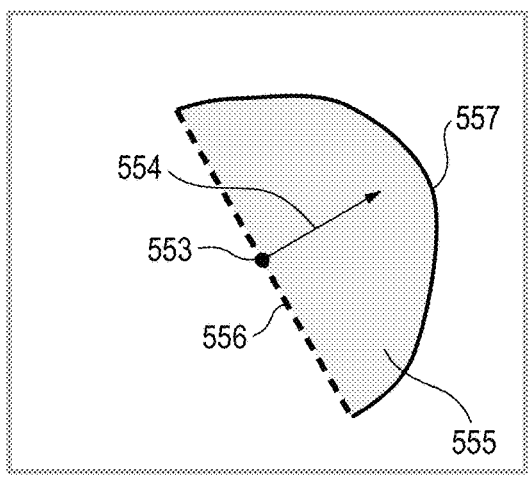
FIG. 8A and FIG. 8B are diagrams for illustrating an example in which the first boundary part is corrected based on a rotated image of the second boundary part.
Figure 8B:
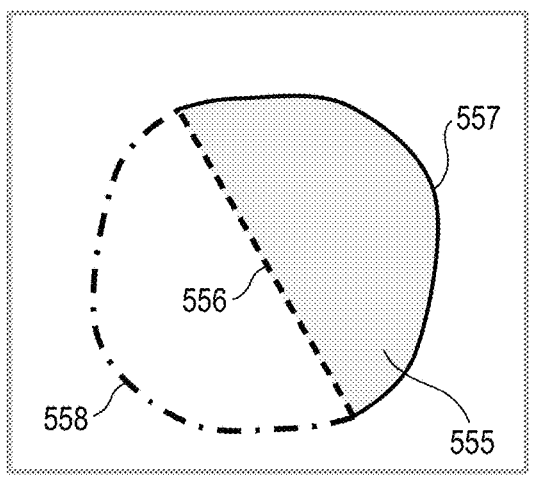

Moreover, FIG. 8A and FIG. 8B are diagrams for illustrating an example in which the attached surface (first boundary part) is corrected based on the rotated image of the non-attached surface (second boundary part). The correction part 1040 rotates an attached surface 548 (plane symmetrical image of the non-attached surface) of FIG. 7B by 180° with a rotation axis 554, which is a normal vector at a center 553 of the surface obtained by approximating an attached surface 556 with a plane, to thereby generate a rotated image. The correction part 1040 connects the rotated image as a non-attached surface 557 to set the rotated image to an attached surface 558 after the correction.

As described above, the correction part 1040 may correct the attached surface (first boundary part) of the target site (first site) in the medical image using at least one of the approximate curve, the approximate curved surface, the symmetrical image, or the rotated image to a shape approximating the non-attached surface (second boundary part), and hence calculate the shape feature amount of the target site more appropriately.

Second Embodiment

Next, an example of a second embodiment of the present invention is described in detail with reference to the drawings. Description on configurations, functions, and operation similar to those of the first embodiment is omitted, and a configuration unique to this embodiment is mainly described.

In the second embodiment, there is described an example including additional processing of determining whether or not to perform processing for correcting the attached surface, based on the attached/non-attached-surface information identified by the boundary identification part 1031 in Step S1131. In this embodiment, it is determined whether or not to perform the correction processing based on the shape feature amount of at least one of the attached surface or the non-attached surface. When it is determined to perform the correction processing, the correction part 1040 corrects the attached surface as in the first embodiment.

Figure 9:
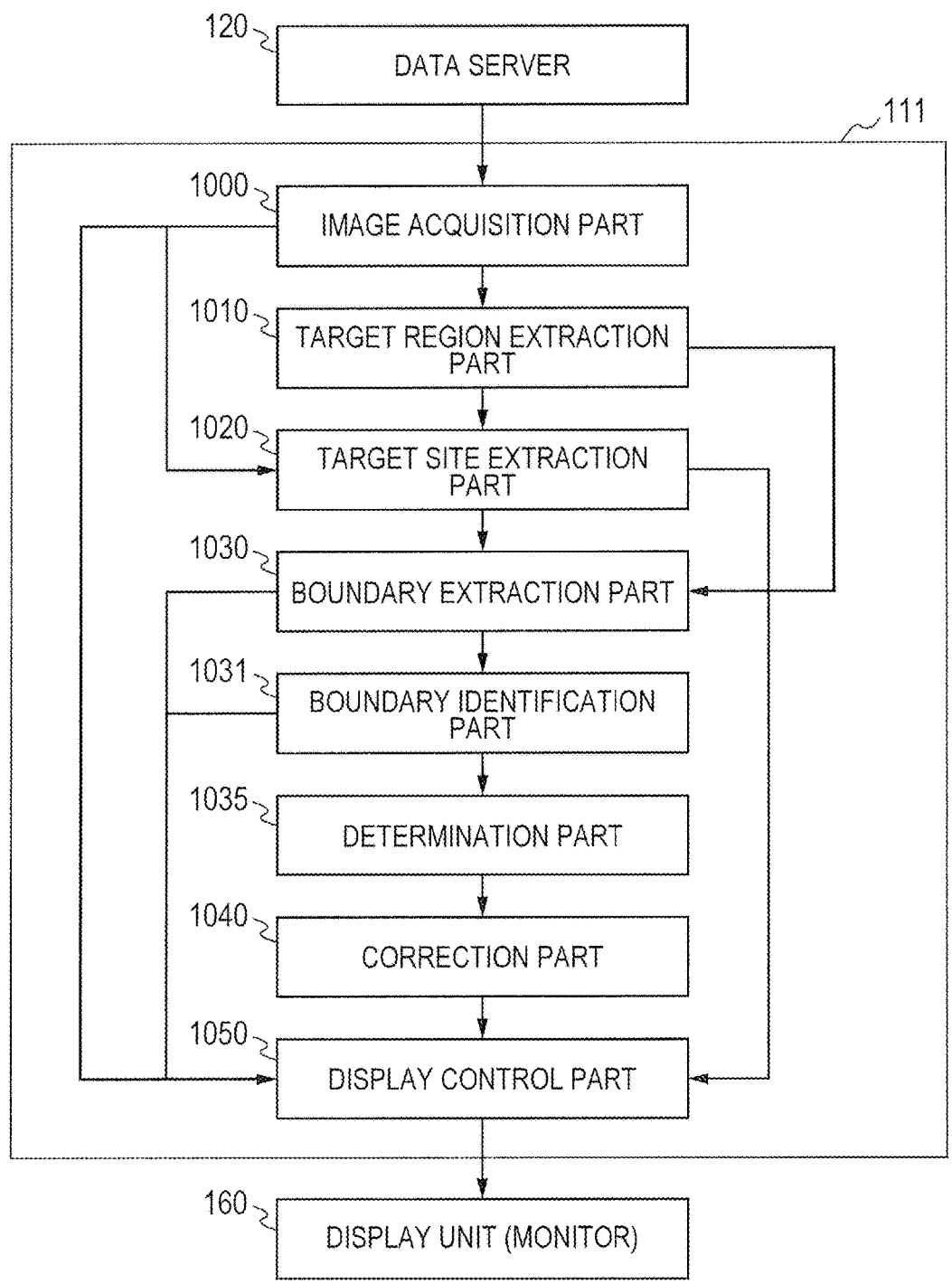
FIG. 9 is a diagram for illustrating a functional configuration of an image processing system including a control unit according to a second embodiment of the present invention.

Next, an apparatus configuration, a functional configuration, and a processing flow are specifically described. FIG. 9 is a diagram for illustrating a functional configuration of an image processing system including a control unit 111 according to this embodiment. As illustrated in FIG. 9, the control unit 111 in this embodiment includes, as functional components, an image acquisition part 1000, a target region extraction part 1010, a target site extraction part 1020, a boundary extraction part 1030, a boundary identification part 1031, a determination part 1035, a correction part 1040, and a display control part 1050.

The determination part 1035 sets a feature amount (shape feature amount) representing at least one feature of the shape of the attached surface (first boundary part) or the non-attached surface (second boundary part) as a determination feature amount, and determines whether or not to correct the shape of the attached surface (first boundary part), based on the determination feature amount. When the determination part 1035 determines that the correction processing is to be performed, the correction part 1040 corrects the shape of the attached part (first boundary part) of the target site based on the non-attached part (second boundary part) of the target site.

Figure 10:
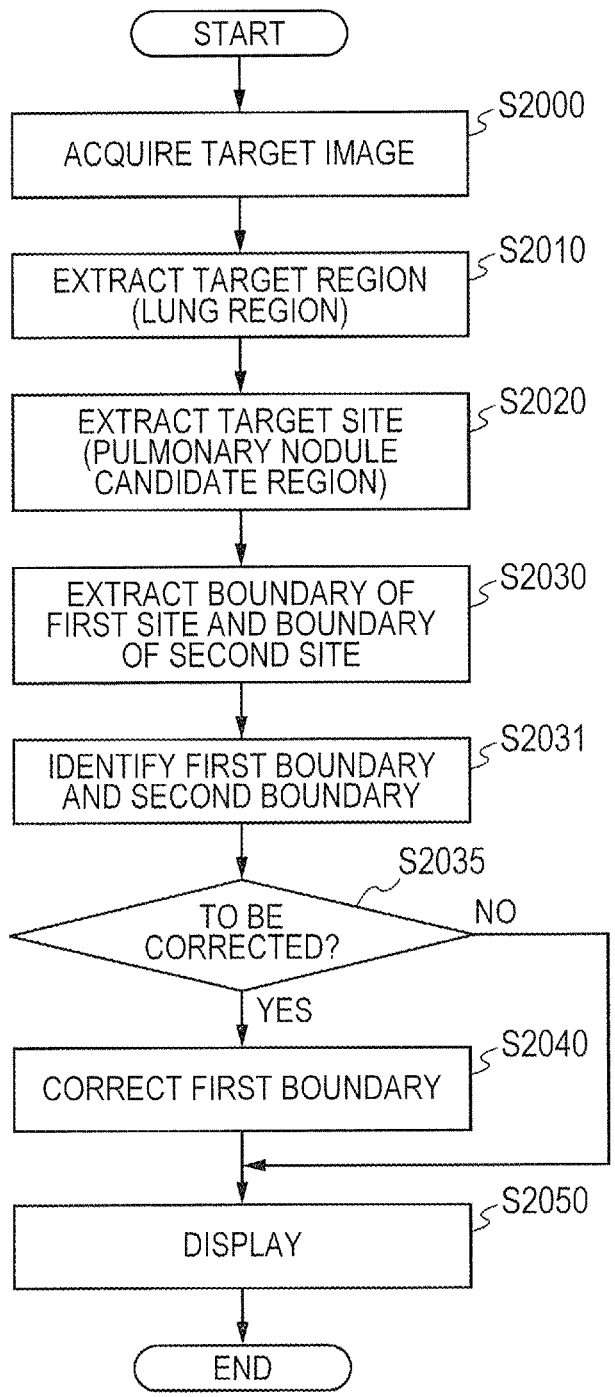
FIG. 10 is a flow chart for illustrating processing executed by an image processing apparatus according to the second embodiment.

Next, operation of an image processing apparatus according to this embodiment is described in detail with reference to FIG. 10. FIG. 10 is a flow chart for illustrating processing executed by the image processing apparatus according to this embodiment. Processing in Steps S2000 to S2030 corresponds to processing in Steps S1100 to S1130 in the first embodiment.

<Step S2035>

In Step S2035, the determination part 1035 determines whether or not to correct the shape of the attached surface (first boundary part), based on the determination feature amount. Here, the determination feature amount is at least one of a length, a tangent, a normal, or a curvature of the attached surface (first boundary part) or of the non-attached surface (second boundary part). Alternatively, the determination feature amount may be at least one of a center of gravity, an area, a volume, a circularity, or a sphericity of the region defined by the attached surface (first boundary part) or of the non-attached surface (second boundary part).

For example, the determination part 1035 compares the determination feature amounts of the attached surface and the non-attached surface, which have been acquired in Step S2030, to determine whether or not to correct the attached surface. The determination part 1035 calculates respective areas of regions defined by the attached surface and the non-attached surface, and calculates a ratio $D_f$ of the areas of the attached surface and the non-attached surface. When $D_f$ is equal to or more than a preset threshold $T_f$, the determination part 1035 determines that the attached surface is to be corrected, and the processing proceeds to Step S2040. In contrast, when $D_f$ is less than the threshold $T_f$, the determination part 1035 determines that the attached surface is not to be corrected, and the processing proceeds to Step S2050.

Figure 11A:
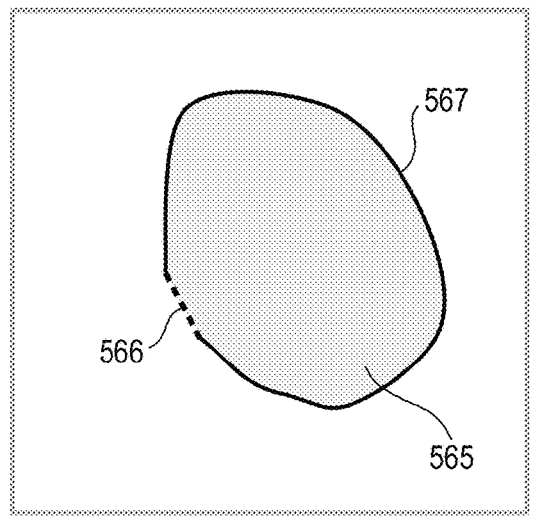
FIG. 11A and FIG. 11B are diagrams for illustrating determination on whether or not a first boundary part needs to be corrected.

As illustrated in FIG. 11A, the determination part 1035 compares an area of an attached surface 566 and an area of a non-attached surface 567 in a pulmonary nodule candidate region (first site) 565 to calculate the ratio $D_f$ of the areas. When the pulmonary nodule candidate region (first site) 565 is hardly attached to the pleura (second site), $D_f$ is less than the threshold $T_f$, and hence the determination part 1035 determines that the attached surface 566 is not to be corrected.

Figure 11B:
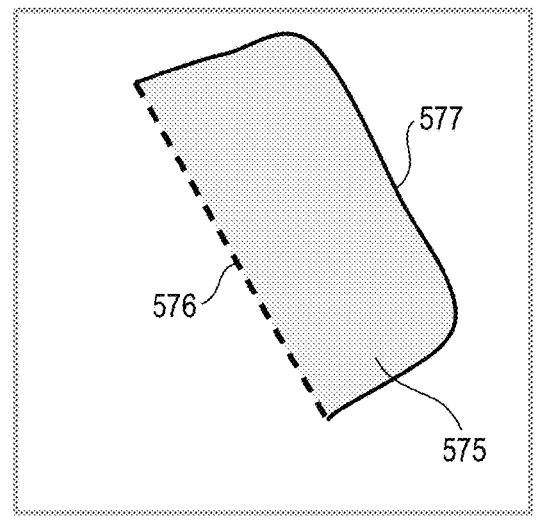

Alternatively, as illustrated in FIG. 11B, the determination part 1035 compares an average curvature of the attached surface 566 and an average curvature of the non-attached surface 567 of the pulmonary nodule candidate region (first site) 565 to calculate a difference $S_f$ between the average curvatures. In a pulmonary nodule candidate region (first site) 575 having a polygonal or polyhedral contour, an average curvature of an attached surface 576 and an average curvature of a non-attached surface 577 are substantially equal to each other (close to 0), and hence the difference $S_f$ is less than the threshold $T_f$, with the result that the determination part 1035 determines that the attached surface 576 is not to be corrected.

Alternatively, the determination part 1035 may compare a length of a cross section of the attached surface with the predetermined threshold $T_f$, or compare a ratio of lengths of cross sections of the attached surface and the non-attached surface with the predetermined threshold $T_f$. Alternatively, the determination part 1035 may generate a histogram of directions of normals of the non-attached surface, and determine whether or not to correct the attached surface based on a distribution of the histogram. Alternatively, the determination part 1035 may determine whether or not to correct the attached surface based on a circularity of the attached surface or on a sphericity of the pulmonary nodule candidate region (region defined by the attached surface and the non-attached surface).

As described above, the determination part 1035 determines the influence the correction of the attached surface (first boundary part) has on the calculation of the shape feature amount used in the computer aided diagnosis. When the influence is small, the attached surface is not corrected so that more efficient processing (processing of calculating the shape feature amount) may be performed without performing unnecessary correction processing.

<Step S2040>

In Step S2040, the correction part 1040 corrects the shape of the attached surface (first boundary part), which has been determined to be corrected, based on the non-attached part (second boundary part). The correction part 1040 corrects the shape of the attached surface of the pulmonary nodule candidate region using the lung region extracted in Step S2010, the pulmonary nodule candidate region extracted in Step S2020, and the attached/non-attached-surface information identified in Step S2031.

<Step S2050>

In Step S2050, the display unit 160 displays at least one of the target site (first site), the site (second site) that is adhere to the target site, or the attached/non-attached-surface information under control of the display control part 1050. When it is determined in Step S2035 that the attached surface is not to be corrected, the display unit 160 may display information indicating that the attached surface has not been corrected.

As described above, the determination part 1035 determines whether or not the attached surface needs to be corrected, based on the determination feature amount so that the more efficient processing (processing of calculating the shape feature amount) may be performed without performing unnecessary correction processing.

Third Embodiment

Next, an example of a third embodiment of the present invention is described in detail with reference to the drawings. Description on configurations, functions, and operation similar to those of the first and second embodiments is omitted, and a configuration unique to this embodiment is mainly described.

In the third embodiment, there is described an example in which the shape of the pulmonary nodule candidate region (first site) is estimated based on shape feature amounts of the attached surface (first boundary part) before and after the correction.

Figure 12:
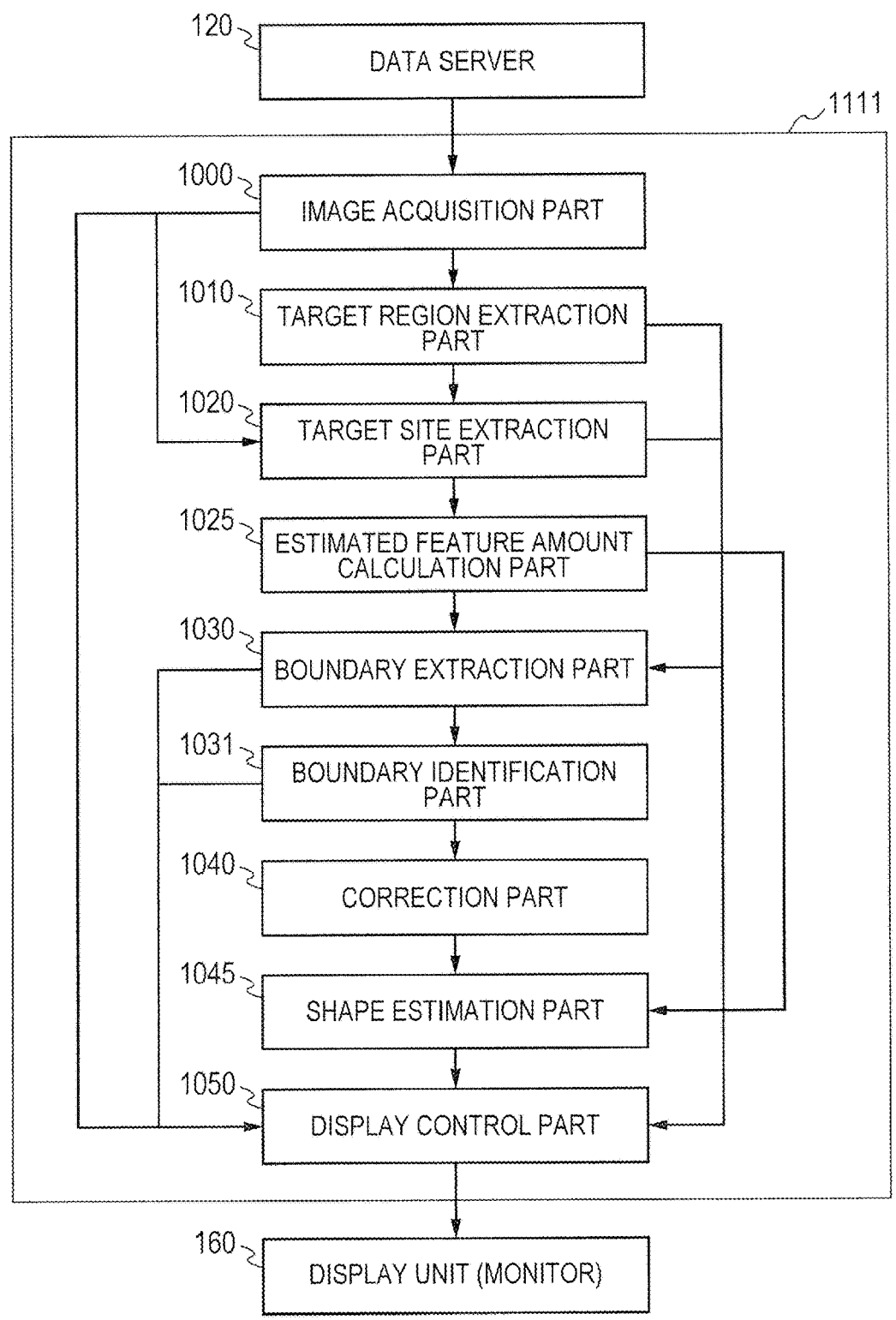
FIG. 12 is a diagram for illustrating a functional configuration of an image processing system including a control unit according to a third embodiment of the present invention.

Next, an apparatus configuration, a functional configuration, and a processing flow are specifically described. FIG. 12 is a diagram for illustrating a functional configuration of an image processing system including a control unit 1111 according to this embodiment. As illustrated in FIG. 12, the control unit 1111 in this embodiment includes, as functional components, an image acquisition part 1000, a target region extraction part 1010, a target site extraction part 1020, an estimated feature amount calculation part 1025, a boundary extraction part 1030, a boundary identification part 1031, a correction part 1040, a shape estimation part 1045, and a display control part 1050.

The estimated feature amount calculation part 1025 is configured to calculate, as an estimated feature amount, a feature amount of the attached surface (first boundary part)

representing a feature of a shape of the boundary of the pulmonary nodule candidate region (first site) before the correction. The shape estimation part 1045 is configured to calculate, as an estimated feature amount, a feature amount of the attached surface (first boundary part) representing at least one feature of the shape of the boundary of the pulmonary nodule candidate region (first site) after the correction. Here, the estimated feature amount before the correction is represented by $f_{before}$, and the estimated feature amount after the correction is represented by $f_{after}$.

The shape estimation part 1045 is configured to set the feature amounts (shape feature amounts) representing the at least one feature of the shape of the boundary of the pulmonary nodule candidate region (first site) before the correction and the boundary of the pulmonary nodule candidate region after the correction as the estimated feature amounts, and to estimate the shape of the pulmonary nodule candidate region based on the estimated feature amounts.

Figure 13:
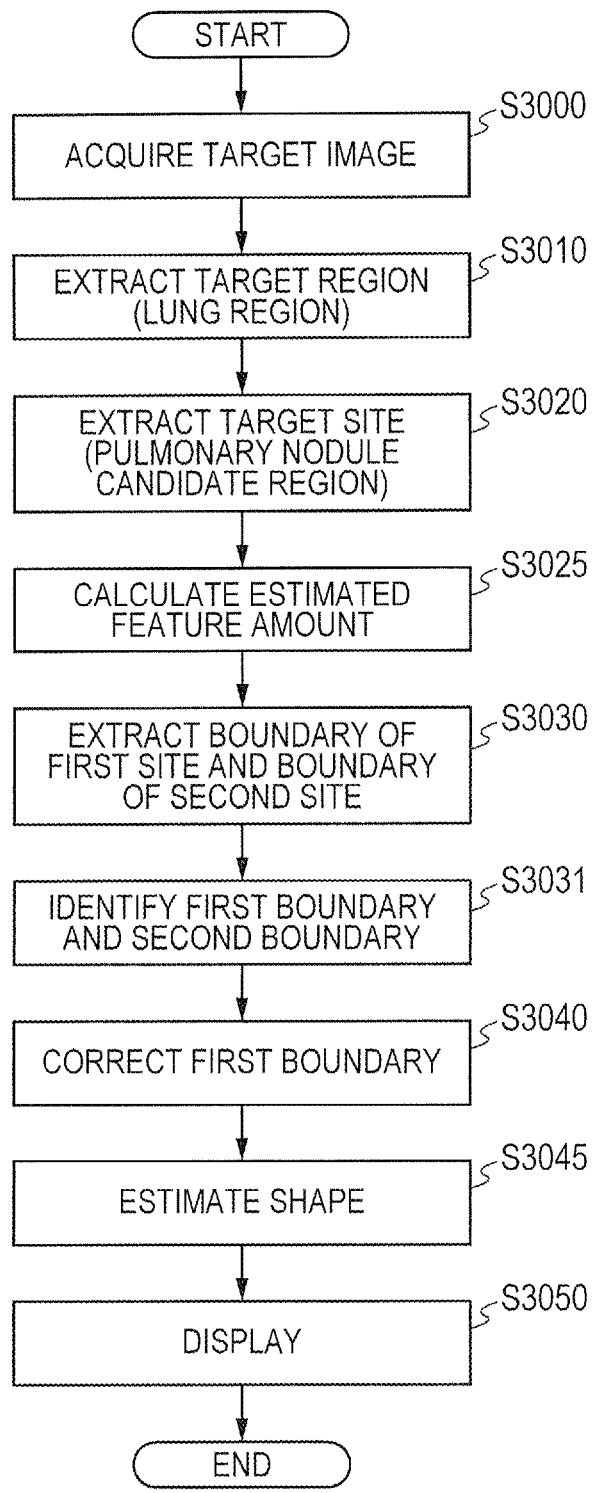
FIG. 13 is a flow chart for illustrating processing executed by an image processing apparatus according to the third embodiment.

Next, operation of an image processing apparatus according to this embodiment is described in detail with reference to FIG. 13. FIG. 13 is a flow chart for illustrating processing executed by the image processing apparatus according to this embodiment. Processing in Steps S3000 to S3020 corresponds to processing in Steps S1100 to S1120 in the first embodiment.

<Step S3025>

In Step S3025, the estimated feature amount calculation part 1025 calculates the estimated feature amount $f_{before}$, which is the shape feature amount of the pulmonary nodule candidate region before the correction, using the density value (pixel value) of the target image acquired in Step S3000 and information on the target site (first site) extracted in Step S3020. Here, the estimated feature amount $f_{before}$ is at least one of a length, a tangent, a normal, a curvature, a center of gravity, an area, a volume, an elongatedness, a circularity, a sphericity, a moment, a Fourier descriptor, or spherical harmonics (SPHARM) of the boundary of the pulmonary nodule candidate S3000 region (first site) before the correction.

<Step S3030>

In Step S3030, the boundary extraction part 1030 extracts the boundary of the target site (first site) and the boundary of the site (second site) that is adhere to the target site to obtain the attached/non-attached-surface information.

<Step S3040>

In Step S3040, the correction part 1040 corrects the shape of the attached part (first boundary part) based on at least one of the approximate curve approximating the non-attached surface (second boundary part), the approximate curved surface approximating the non-attached surface (second boundary part), the symmetrical image of the non-attached surface (second boundary part), or the rotated image of the non-attached surface (second boundary part). The correction part 1040 may select the at least one of the approximate curve, the approximate curved surface, the symmetrical image, or the rotated image for correcting the shape of the attached part (first boundary part), based on the estimated feature amount $f_{before}$ calculated in Step S3025.

For example, the estimated feature amount calculation part 1025 calculates, as the estimated feature amounts $f_{before}$, an area (attached area) of a surface obtained by approximating the attached surface $S_{attached}$ with a plane and a cross-sectional area (cross-section) of the pulmonary nodule candidate region (first site) taken along a plane parallel to the surface. When the attached area is larger than any cross-sectional area, that is, the attached area is largest at the first site, the correction part 1040 selects the symmetrical image or the rotated image of the non-attached surface (second boundary part), and corrects the shape of the attached part (first boundary part) based on the selected symmetrical image or rotated image.

<Step S3045>

In Step S3045, the shape estimation part 1045 calculates the estimated feature amount $f_{after}$, which is the shape feature amount of the pulmonary nodule candidate region (first site) after the correction, using the information on the target site (first site) corrected in Step S3040. Moreover, the shape estimation part 1045 estimates the shape of the pulmonary nodule candidate region (first site) based on estimated feature amounts $f_{before}$ and $f_{after}$ before and after the correction.

Here, the estimated feature amount $f_{after}$ is at least one of a length, a tangent, a normal, a curvature, a center of gravity, an area, a volume, an elongatedness, a circularity, a sphericity, a moment, a Fourier descriptor, or spherical harmonics (SPHARM) of the boundary of the pulmonary nodule candidate region (first site) after the correction.

For example, the shape estimation part 1045 compares the estimated feature amounts $f_{before}$ and $f_{after}$ before and after the correction to estimate the shape of the pulmonary nodule candidate region (first site). The shape estimation part 1045 estimates the shape of the pulmonary nodule candidate region (first site) based on the estimated feature amounts $f_{before}$ and $f_{after}$ before and after the correction, and on a difference $f_{sub}$ between the estimated feature amounts $f_{before}$ and $f_{after}$.

Figure 14A:
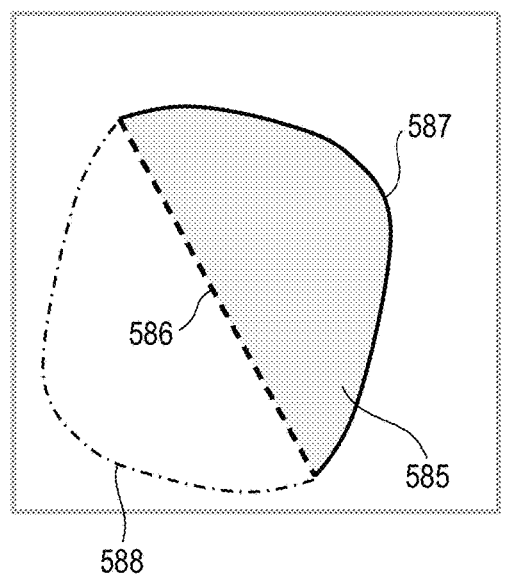
FIG. 14A and FIG. 14B are diagrams for illustrating estimation of a shape of a first site.

As illustrated in FIG. 14A, the estimated feature amount calculation part 1025 sets the sphericity of the pulmonary nodule candidate region (first site) 585 before the correction as the shape feature amount to calculate the estimated feature amount $f_{before}$. A region defined by the non-attached surface 587 is semispherical, and hence the estimated feature amount (sphericity) $f_{before}$ is 0.5 or less.

The shape estimation part 1045 calculates, as the estimated feature amount $f_{after}$, a sphericity of the pulmonary nodule candidate region (first site) 585 after the correction. As a result of the correction, an attached surface 586 is extended to an attached surface 588 to the pulmonary nodule candidate region after the correction spherical, and hence the estimated feature amount (sphericity) $f_{after}$ is 0.8 or more. In this case, the shape estimation part 1045 estimates that the non-attached surface 587 is semispherical based on the estimated feature amounts $f_{before}$ and $f_{after}$ before and after the correction.

Figure 14B:
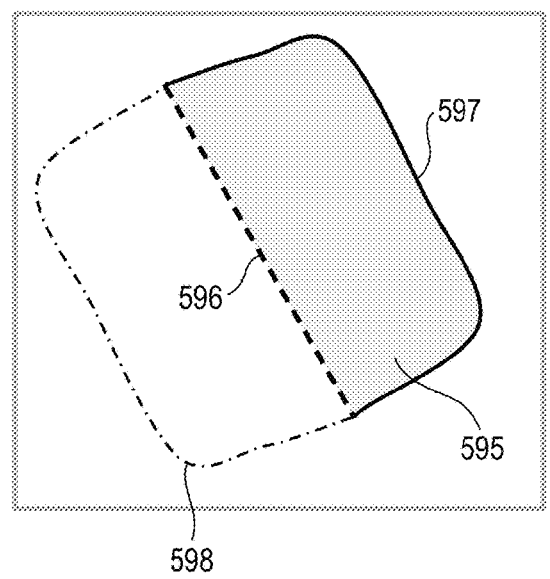

Moreover, as illustrated in FIG. 14B, the estimated feature amount calculation part 1025 sets a sphericity of a pulmonary nodule candidate region (first site) 595 before the correction as the shape feature amount to calculate the estimated feature amount $f_{before}$. A non-attached surface 597 is rectangular parallelepiped, and hence the estimated feature amount (sphericity) $f_{before}$ is 0.5 or less.

The shape estimation part 1045 calculates, as the estimated feature amount $f_{after}$, a sphericity of a pulmonary nodule candidate region (first site) 595 after the correction. As a result of the correction, an attached surface 596 is extended to an attached surface 598 to make the pulmonary nodule candidate region after the correction rectangular parallelepiped or cubic, and hence the estimated feature amount (sphericity) $f_{after}$ is 0.5 or less. Moreover, the sphericities before and after the correction are substantially the equal to each other, and hence the difference $f_{sub}$ between the estimated feature amounts $f_{before}$ and $f_{after}$ is a predetermined threshold or less. In this case, the shape estimation part 1045 estimates that a non-attached surface 597 is rectangular parallelepiped (polyhedral) based on the estimated feature amounts $f_{before}$ and $f_{after}$ before and after the correction, and on the difference $f_{sub}$.

Alternatively, the shape estimation part 1045 may generate a histogram of directions of normals of the non-attached surface, and estimate the shape of the pulmonary nodule candidate region (first site) based on a distribution of the histogram. Alternatively, the shape estimation part 1045 may estimate the shape of the pulmonary nodule candidate region (first site) based on a change in cross-sectional areas of the pulmonary nodule candidate region (first site) taken along a plurality of parallel planes. Alternatively, the shape estimation part 1045 may estimate the shape of the pulmonary nodule candidate region (first site) based on a shape vector of the spherical harmonics (SPHARM).

Alternatively, the shape estimation part 1045 may estimate the shape of the above-mentioned first site by pattern recognition. When the pulmonary nodule candidate region included as the attached abnormal shadow in the medical image is to be classified into categories, such as sphere-like objects or polygonal, the shape estimation part 1045 sets shape feature amounts belonging to the respective categories as learning data in advance, and generates a discriminative model using the estimated feature amounts $f_{before}$ and $f_{after}$ and the difference $f_{sub}$. The shape estimation part 1045 uses the discriminative model for pattern recognition to estimate the shape of the pulmonary nodule candidate region (first site).

<Step S3050>

In Step S3050, the display unit 160 displays at least one of the target site (first site), the site (second site) that is adhere to the target site, the attached/non-attached-surface information, the estimation result of the shape of the target site (first site), the estimated feature amounts $f_{before}$ and $f_{after}$, or the difference $f_{sub}$ under control of the display control part 1050.

As described above, the shape estimation part 1045 estimates the shape of the pulmonary nodule candidate region (first site) so that the estimated shape is an indicator in the processing for distinguishing benignancy and malignancy of the pulmonary nodule. Moreover, the shape feature amount and the estimated feature amounts of the region of the attached abnormal shadow, which have been calculated by the CAD, may be compared to determine whether or not the correction by the correction part 1040 has been appropriate. Further, the estimated shape may be used as a new feature amount in the CAD.

In another embodiment of the present invention, it is determined whether or not the target region, such as the pulmonary nodule candidate region, includes the attached part, and when it is determined that the attached part is included, the shape of the target region including the attached part is corrected. In this case, as in the first embodiment, for the target region extracted by the target region extraction part 1010, the boundary between the target region and the site, such as an organ or blood vessels, that is adhere to the target region is extracted by the boundary extraction part 1030. Then, the boundary identification part 1031 identifies, as the first boundary part (attached part), the partial boundary of the target site (first site) that is adhere to the boundary of the site (second site) that is adhere to the target site. At this time, when the attached part is identified by the boundary identification part 1031, the boundary identification part 1031 determines that there is an attached part. When the determination is made, the correction part 1040 corrects the shape of the attached part (first boundary part) of the target site based on the non-attached part (second boundary part) of the target site. Here, when no attached part is identified by the boundary identification part 1031, the correction part 1040 does not perform the above-mentioned correction processing.

The display control part 1050 outputs, to the display unit 160, the information on the pulmonary nodule candidate region extracted by the target site extraction part 1020, the site that is adhere to the pulmonary nodule candidate region, the attached surface and the non-attached surface of the pulmonary nodule candidate region, which have been identified by the boundary identification part 1031, and the attached surface corrected by the correction part 1040. Here, when the correction has been performed by the correction part 1040, information indicating that the correction has been performed may be output. Moreover, when the correction has been performed by the correction part 1040, the display control part 1050 may cause the shape after the correction to be displayed in a form of being superimposed on the target region. Moreover, for example, the display of the boundary of the target region after the correction and the display of the boundary of the target region before the correction may be displayed switchably. Alternatively, information indicating a position of the first boundary part (attached part) and information indicating the shape after the correction may be superimposed on the target image to establish a state in which activity indication is displayed.

Moreover, when the correction has not been performed by the correction part 1040, information indicating that the correction has not been performed may be output.

Moreover, in another embodiment of the present invention, the display control part 1050 may cause the target image to be displayed, cause the first boundary part (attached part) and the non-attached part (second boundary part), which have been identified by the boundary identification part 1031, to be superimposed on the target region of the target image for display, and allow the first and second boundary parts to be changed in response to an operation input from operation units, such as the mouse 170 and the keyboard 180. When the first or second boundary part has been changed in response to the operation input, the processing for correcting the shape by the correction part 1040 and the determination processing by the determination part 1035 are performed based on the boundary part after the change. When the change in response to the operation input has been made after the processing for correcting the shape by the correction part 1040 or the determination processing by the determination part 1035, the correction part 1040 and the determination part 1035 respectively perform the correction processing and the determination processing again.

The shape corrected in the processing according to the embodiments described above is used in the processing for deriving image findings of the target site. The image findings are, for example, text information that is given by an image diagnostic doctor and indicates evaluations on a lesion and the like. In one of the embodiments, such image findings are automatically derived by the system. For example, morphological image findings on a general shape of the target site, such as sphere-like objects or lobular, and on a contour line, such as smooth or convex, are derived using the shape feature amount calculated from the target site (first site) after the above-mentioned correction. With the above-mentioned correction processing, the image findings may be derived more correctly as compared to a case where the correction processing is not performed. The derivation processing is achieved by using mapping with a reference value to which the shape feature amount has been set in advance, classification by machine learning, and other such technologies, for example. The morphological image findings are used as important bases in the image diagnosis, and hence are expected to improve the accuracy in diagnosis of the lesion.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-151611, filed Jul. 31, 2015, which is hereby incorporated by reference herein in its entirety.

What is claimed is:

1. An image processing apparatus, comprising:
   a boundary extraction unit configured to extract a boundary of a first site and a boundary of a second site in a medical image;
   a boundary identification unit configured to identify a partial boundary of the first site that is adhered to the boundary of the second site as a first boundary part of the first site, and to identify a partial boundary of the first site that is not adhered to the boundary of the second site as a second boundary part of the first site; and
   a correction unit configured to correct a shape of the first boundary part of the first site so that the shape of the first boundary part of the first site has symmetry with a shape of the second boundary part of the first site.

2. An image processing apparatus according to claim 1, wherein the correction unit is configured to correct the shape of the first boundary part with an active contour model that is based on a shape of at least a part of the second boundary part.

3. An image processing apparatus according to claim 1, wherein the correction unit is configured to correct the shape of the first boundary part based on at least one of an approximate curve approximating the second boundary part, an approximate curved surface approximating the second boundary part, a symmetrical image of the second boundary part, or a rotated image of the second boundary part.

4. An image processing apparatus according to claim 1, further comprising a determination unit configured to set a feature amount representing at least one feature of a shape of the first boundary part or the second boundary part as a determination feature amount, and to determine whether or not to correct the shape of the first boundary part based on the determination feature amount.

5. An image processing apparatus according to claim 4, wherein the determination unit is configured to set at least one of a length, a tangent, a normal, or a curvature of one of the first boundary part and the second boundary part, and a center of gravity, an area, a volume, a circularity, or a sphericity of a region defined by one of the first boundary part and the second boundary part as the determination feature amount, and to determine whether or not to correct the shape of the first boundary part.

6. An image processing apparatus according to claim 1, further comprising a shape estimation unit configured to set feature amounts representing at least one feature of shapes of the boundary of the first site before the correction and the boundary of the first site after the correction as estimated feature amounts, and to estimate a shape of the first site based on the estimated feature amounts.

7. An image processing apparatus according to claim 6, wherein the shape estimation unit is configured to set at least one of lengths, tangents, normals, curvatures, centers of gravity, areas, volumes, elongatednesses, circularities, sphericities, moments, Fourier descriptors, or spherical harmonics of the boundary of the first site before the correction and the boundary of the first site after the correction as the estimated feature amounts, and to estimate the shape of the first site.

8. An image processing apparatus according to claim 6, wherein the shape estimation unit is configured to estimate the shape of the first site by pattern recognition.

9. An image processing apparatus according to claim 1, wherein at a contact boundary between the first boundary part of the first site and the second boundary part of the first site, the shape of the first boundary part of the first site is corrected such that smoothness of the contour at the contact boundary is maintained.

10. An image processing method, comprising:
    extracting a boundary of a first site and a boundary of a second site in a medical image;
    identifying a partial boundary of the first site that is adhered to the boundary of the second site as a first boundary part of the first site, and identifying a partial boundary of the first site that is not adhered to the boundary of the second site as a second boundary part of the first site; and
    correcting a shape of the first boundary part of the first site so that the shape of the first boundary part of the first site has symmetry with a shape of the second boundary part of the first site.

11. A non-transitory computer-readable storage medium having stored thereon a program for causing a computer to execute an image processing method, the image processing method comprising:
    extracting a boundary of a first site and a boundary of a second site in a medical image;
    identifying a partial boundary of the first site that is adhered to the boundary of the second site as a first boundary part of the first site, and identifying a partial boundary of the first site that is not adhered to the boundary of the second site as a second boundary part of the first site; and correcting a shape of the first boundary part of the first site so that the shape of the first boundary part of the first site has symmetry with a shape of the second boundary part of the first site.

12. An image processing method, comprising:

extracting a boundary of a first site and a boundary of a second site in a medical image;

identifying a partial boundary of the first site that is adhered to the boundary of the second site as a first boundary part of the first site, and identifying a partial boundary of the first site that is not adhered to the boundary of the second site as a second boundary part of the first site; and correcting a shape of the first boundary part of the first site for symmetry with a shape of the second boundary part of the first site.

* * * * *